United States Patent [19]

Pookote et al.

[11] 4,454,361
[45] Jun. 12, 1984

[54] CRYSTAL PURIFICATION

[75] Inventors: Suseelan R. Pookote, Chesterfield; Melvin R. Bagley, St. Louis, both of Mo.

[73] Assignee: Monsanto Company, St. Louis, Mo.

[21] Appl. No.: 448,653

[22] Filed: Dec. 10, 1982

[51] Int. Cl.³ .............................................. C07C 79/12
[52] U.S. Cl. ................................................... 568/937
[58] Field of Search ......................................... 568/937

[56] References Cited

U.S. PATENT DOCUMENTS 3,113,161 12/1963 Schmalenbach .................... 260/674
3,832,410 8/1974 Hug et al. ............................ 568/937
3,880,942 4/1975 Hug et al. ............................ 568/937

Primary Examiner—Leland A. Sebastian
Attorney, Agent, or Firm—Wendell W. Brooks; James C. Logomasini; Arnold H. Cole

[57] ABSTRACT

Mixtures of para-nitrochlorobenzene crystals and a liquid, ordinarily comprising the mother liquor of the crystals are continuously separated in one or more cylindrical presses in at least two stages. Reduction of the interstitial space causes the mother liquor to be forced out of the drainage aperatures thus purifying the crystals.

18 Claims, 1 Drawing Figure

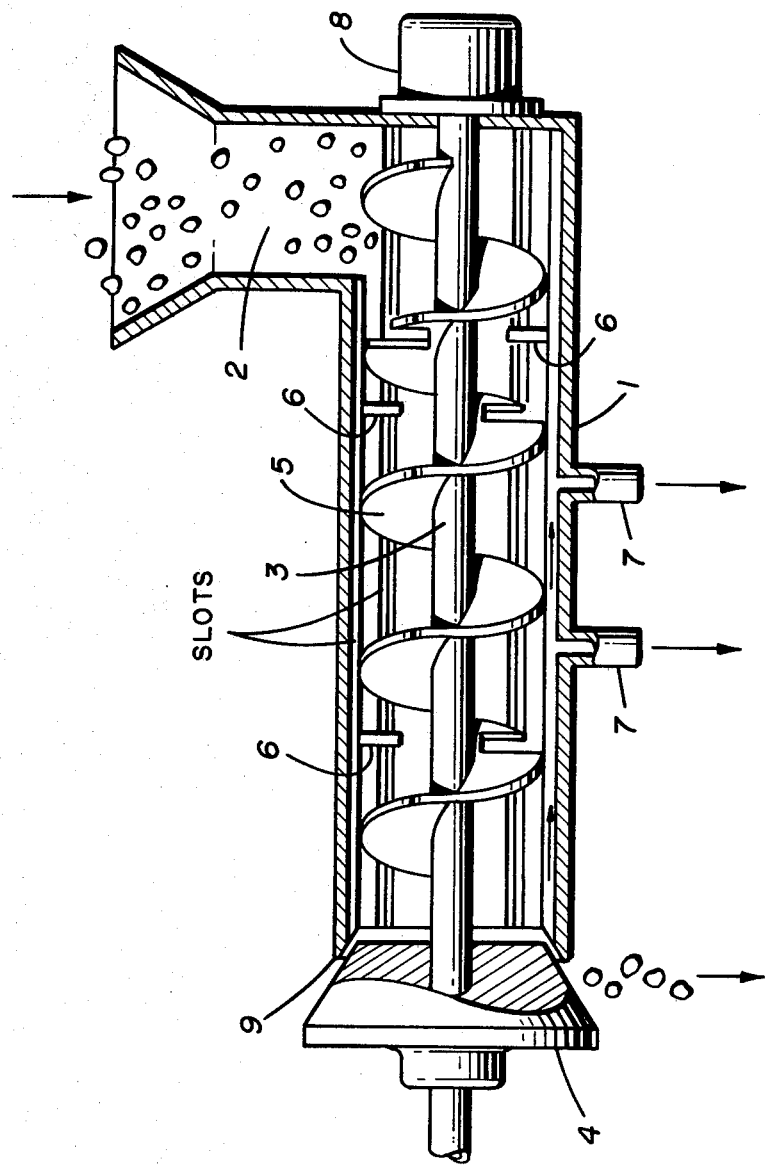

CRYSTAL PURIFICATION

BACKGROUND OF THE INVENTION

1. Field of the Invention

The invention relates to separation and purification, particularly separation of crystals of an aromatic organic compound, particularly para-nitrochlorobenzene, from a mother liquor.

2. Description of the Prior Art

In the commercial purification of aromatic organic compounds by crystallization, mechanical techniques such as filtration, decantation or centrifuge are used to remove as much as possible of the adhering mother liquor from the crystals. Residual mother liquor after centrifuging is ordinarily in the range of about 2–5% or more of the weight of crystals. Large uniform crystals from low-viscosity mother liquors will retain a minimum proportion of mother liquor. Non-uniform small crystals from viscous solutions will retain a considerably larger proportion. It is common practice to wash crystals on a centrifuge or to filter with a fresh solvent; and the use of counter current washing in multiple stages is known to reduce the loss of crystals by solution in the solvent. The use of a solvent requires separate steps to remove residual solvent from the product such as by drying and some means of solvent recovery. Batch press squeeze purification has been employed commercially but its lack of continuity of operation has been a serious handicap. U.S. Pat. No. 3,113,161 teaches the use of a screw press purifier in the production of naphthalene.

In the commercial production of nitrochlorobenzene, the mother liquor ordinarily contains nitrochlorobenzene isomers, trace organic impurities and trace amounts of water. This mother liquor will have ordinarily been pretreated to remove most inorganic acids, monochlorobenzene and water prior to the purification contemplated herein. Any improved method of purifying would be a significant advance in the art and is an object of this invention.

SUMMARY OF THE INVENTION

According to this invention a continuous multiple stage separation of a feed mixture of crude para-nitrochlorobenzene (PNCB) is provided where the feed mixture comprises about 50–100 (preferably 90–100) weight percent of the PNCB crystals containing small amounts of both intra-crystalline and inter-crystalline mother liquor (hereafter called "crude crystals") and about 0–50 (preferably 0–10) weight percent of the same mother liquor comprising nitrochlorobenzene (NCB) isomers and traces of organic materials and water (hereafter called "extra-crystalline liquid"). The process comprises continuously feeding the mixture into one or more cylindrical presses having a feed orifice, a substantially closed compression channel with drainage means and an ejection orifice thereby subjecting the mixture to at least two stages of temperature and/or pressure and for maximum purification efficiency should be as close as possible to the melting point of PNCB (83.5° C.). In each stage the mixture is subjected to a pressure sufficient to substantially reduce interstitial space between crystals while maintaining the crystals at a temperature below their melting point. In each successive stage the temperature is increased substantially over the temperature of the preceding stage. In each stage a substantial portion of the liquid flows in the compression chamber both radially and axially countercurrent to the flow of solids. The reverse axial flow pattern of the liquid contributes to the purification by a washing action. The main purification mechanism is the expulsion of liquid by compression. The liquid is caused to be drained and removed leaving in the compression channel a purified crystal with compressed interstitial space. The purified crystal is continuously ejected from the closed compression chamber.

A stage may be separated from a subsequent stage by using separate screw extruders for each stage. One or more separate stages may also be incorporated into a single screw extruder.

By "cylindrical press" is meant any press in which compression is effected within a cylinder. Such a press may be of the conventional screw type, a continuous circular channel, or any other such press having continuity of operation. Continuity of operation requires continuous feed and ejection.

By "continuous screw type" or "screw type press" is meant any press in which force is applied continuously or discontinuously to a material within a generally cylindrical chamber from an entry end to an exit end, along a generally spiral path by a turning, continuous screw or discontinuous screw type segment, as against opposing forces created by obstacles along the path of the screw or segments thereof and/or near the exit end of the cylinder. By "generally cylindrical" is meant to include tapered or conical chambers in which the exit end is of a smaller diameter than the entry end as well as cylinders with other than circular cross-sections.

In the detailed description, reference will be made to the drawing in which the FIGURE is a schematic section of a preferred screw-type cylindrical press suitable for the practice of the process of the instant invention.

DETAILED DESCRIPTION OF A PREFERRED EMBODIMENT

Referring now to the drawing, a preferred screw-type press is comprised of barrel 1 with feed orifice 2 and exit orifice 9. Within barrel 1 is screw 5 mounted on screw axle 3. Axle 3 is turned by drive motor 8. Liquid aperatures 7 are provided for drainage. Within barrel 1 are breaker bars 6 which are spaced intermittently along screw 5. The purpose of the breaker bars is to create discontinuous flow.

In operation, a feed mixture of crude PNCB crystals with or without extra-crystalline liquid are fed into entry orifice 2 and thereafter passed into barrel 1. Screw 5 creates pressure within the barrel which is controlled by adjustable choke 4 so as to regulate the amount of crystals being extruded through exit orifice 9. The liquid in the interstitial spaces is forced out through drainage orifice 7. Drive motor 8 provides the force for turning continuous screw 5 on axle 3. The speed of screw 5 and adjustable choke 4 can be adjusted to obtain optimum pressure for purification and throughput with minimum energy usage.

As stated above, a feed mixture suitable for the practice of this invention employing the particular apparatus described is about 50–100 (preferably 90–100) weight percent crude crystals and about 0–50 (preferably 0–10) weight percent extra crystalline liquid. There is no upper limitation on concentration of crude crystals, but if there is no extra-crystalline liquid, the crude crystals must contain sufficient intra-crystalline and inter-crystalline liquid to make separation a justifiable operation and to provide any lubrication necessary for the particular press design in conjunction with the particular crystal composition. If the amount of crude crystals is less than about 50%, a prior decantation or other separation process step should ordinarily be used so as to make practical the use of the process of this invention. An excess of liquid will ordinarily lower the efficiency and increase the number of pressing cycles required. Of course screw press designs may efficiently accommodate a higher percentage of liquid.

Any crude PNCB crystals may be purified in accordance with this invention. A typical crude PNCB stream has the following composition by weight:
70% PNCB
29% Orthonitrochlorobenzene
1% Metanitrochlorobenzene trace organic impurities
A starting concentraion of PNCB crystals of 90–98% is preferred.

Temperature control, as indicated above, is important because the pressure of and friction created by a screw type press will cause temperatures to rise, often above the melting point of the crystals involved. Control of temperature of the barrel can be maintained by exposing the outer portion thereof to a cold liquid or gas, by circulation of a cold liquid through cooling coils or circulation channels within the chamber, or by other appropriate means. The screw may also be water cooled. While it may be desirable to permit a small percentage of crystals to melt during squeeze purification so as to achieve a wash effect, most crystals should not melt. The temperature of PNCB crystals in the first stage should be about 5°–80° C. with 25°–35° C. being preferred. In the first stage the feed mixture is separated into a NCB lean fraction and a NCB rich fraction. The rich fraction is fed to a second stage operated at a temperature at least 5° higher than the first stage and at about 60°–85° C. with 60°–70° C. being preferred. The temperatures specified are exit temperatures. Interior temperatures may be slightly higher. Temperatures oridinarily increase as the material progresses through the press. The second stage produces a rich product stream and a lean stream which can be cooled, crystallized and recycled to the first stage.

Pressures within a press should ordinarily be of the order to about 500–20,000 psi ($3447 \times 10^3 - 137894 \times 10^3$ N/m$^2$), with pressure of 5000–6000 psi ($34470 \times 10^3 - 41368 \times 10^3$ N/m$^2$) being preferred in the purification of organic aromatic compounds such as those listed above. The pressures applied should be the minimum necessary to achieve the degree of purification needed, and subject to temperature requirements, there is no maximum limitation.

EXAMPLE

Crude nitrochlorobenzene containing approximately 70% para-nitrochlorobenzene, 29% orthonitrochlorobenzene and 1% metanitrochlorobenzene was fed into a flaker operated at 25°–30° C. The flakes were conveyed first to a screw-type press of the type described above. Out of the drainage aperatures of the type described above. Out of the drainage aperatures of the screw-type press came a lean para-nitrochlorobenzene fraction containing approximately 40% para-nitrochlorobenzene, and this fraction was subsequently distilled and reintroduced into the first screw-type press. A second rich fraction was emitted through exit orifice 9. The fraction contained 90–95% para-nitrochlorobenzene, and it was fed into a second screw press which was operated at a temperature of about 65° C. A rich product stream from the second screw press contained about 99.5% para-nitrochlorobenzene. A lean fraction contained 75–80% para-nitrochlorobenzene. This lean stream was recycled to the flaker, and the rich stream was recovered as the product.

We claim:

1. A process for the continuous separation of a feed mixture of para-nitrochlorobenzene crystals and a liquid, the mixture comprising about 50–100 weight percent crude crystals and about 0–50 weight percent extra-crystalline liquid, the process comprising continuously feeding the mixture into at least one cylindrical press having a feed orifice, a substantially closed compression channel having drainage means and an ejection orifice, thereby subjecting the mixture in a first stage and at least one subsequent stage to pressure sufficient to substantially reduce interstitial space bewteen crystals while maintaining the crystals at temperatures below their melting point, causing backflow, drainage and removal of a substantial portion of the liquid leaving in the compression channel a purified crystal with compressed interstitial space; and continuously ejecting the purified crystal, the temperature of the crystals in the first stage being maintained at about 5°–80° C., the temperature of the crystals in at least one subsequent phase being maintained at a temperature at least 5° higher than the first stage and in the range of 60°–85° C.

2. The process of claim 1 where the feed mixture comprises 90–100 weight percent crude crystals and 0–10 weight percent extra-crystalline liquid.

3. The process of claim 1 wherein the operating temperature of the first stage is 25°–35° C.

4. The process of claim 1 wherein the operating temperature of the second stage is 60°–70° C.

5. The process of claim 1 wherein the pressure in the first stage is 500–20,000 psi.

6. The process of claim 1 wherein the pressure in the first stage is 5,000–6,000 psi.

7. The process of claim 1 wherein the pressure in the second stage is 500–20,000 psi.

8. The process of claim 1 wherein the pressure in the second stage is 5,000–6,000 psi.

9. The process of claim 1 wherein the two phases are conducted in separate cylindrical presses.

10. The process of claim 9 wherein the cylindrical presses are screw-type presses.

11. A two stage process by the continuous separation of a feed mixture of para-nitrochlorobenzene crystals and a liquid, the mixture comprising about 50–100 weight percent crude crystals and about 2–50 weight percent extra-crystalline liquid, the process comprising continuously feeding the mixture into a first screw type press having a feed orifice, a substantially closed compression channel having drainage means and an ejection orifice, thereby subjecting the mixture to a pressure sufficient to substantially reduce interstitial space between crystals while maintainingg the crystals at a temperature of 5°–80° C., causing drainage and removal of a substantial portion of the liquid leaving in the compression channel a purified crystal with compressed interstitial space; and continuously ejecting the purified crystals and continuously feeding the ejected purified cyrstals from the first screw-type press into a second screw-type press having a feed orifice, a substantially closed compression channel having drainage means and an ejection orifice, thereby subjecting the once purified crystals to a pressure sufficient to further reduce interstitial space between crystals while maintaining the crystals at a temperature of 60°-85° C. and at least 5° above the operating temperature of the first screw-type press, causing drainage of an additional portion of the liquid leaving in the compression channel a further purified crystal with compressed interstitial spaces and continuously ejecting the further purified crystal.

12. The process of claim 11 where the feed mixtures comprises 90-100 weight percent crude crystals and 0-10 weight percent extra-crystalline liquid.

13. The process of claim 11 wherein the operating temperature of the first screw-type press is 25°-35° C.

14. The process of claim 11 wherein the operating temperature of the second screw-type press is 60°-70° C.

15. The process of claim 11 wherein the pressure in the first screw-type press is 500-20,000 psi.

16. The process of claim 11 wherein the pressure in the first screw-type press is 5,000-6,000 psi.

17. The process of claim 11 wherein the pressure in the second screw-type press is 500-20,000 psi.

18. The process of claim 11 wherein the pressure in the second screw-type press is 5,000-6,000 psi.

* * * * *

UNITED STATES PATENT AND TRADEMARK OFFICE
CERTIFICATE OF CORRECTION

PATENT NO. : 4,454,361

DATED : JUNE 12, 1984

INVENTOR(S) : SUSEELAN R. POOKOTE, MELVIN R. BAGLEY

It is certified that error appears in the above-identified patent and that said Letters Patent is hereby corrected as shown below:

Column 3, lines 60-61, ending with "above.", delete "Out of the drainage aperatures of the type described above."

Column 3, line 61, delete "aperatures" and substitute therefor --aperture--.

Column 4, line 58, delete "maintainingg" and substitute therefor --maintaining--.

Signed and Sealed this

Twenty-third Day of April 1985

[SEAL]

Attest:

DONALD J. QUIGG

Attesting Officer     Acting Commissioner of Patents and Trademarks